United States Patent
Al-Dughaiter et al.

(10) Patent No.: US 11,225,444 B2
(45) Date of Patent: Jan. 18, 2022

(54) METHOD OF COLUMN CONTROL

(71) Applicant: SABIC GLOBAL TECHNOLOGIES B.V., Bergen op Zoom (NL)

(72) Inventors: Abdullah Saad Al-Dughaiter, Riyadh (SA); Shahid Azam, Riyadh (SA); Abdulmajeed Mohammed Al-Hamdan, Riyadh (SA); Dafer Mubarak Alshahrani, Riyadh (SA); Ralf Noack, Dresden (DE); Tobias Meier, Dresden (DE); Gabriel Waurick, Dresden (DE); Heinz Bolt, Wolfratshausen (DE); Andreas Meiswinkel, Prien (DE); Wolfgang Müller, Munich (DE); Anina Wohl, Munich (DE); Hans-Jorge Zander, Munich (DE)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 182 days.

(21) Appl. No.: 16/471,063

(22) PCT Filed: Dec. 19, 2017

(86) PCT No.: PCT/IB2017/058172
§ 371 (c)(1),
(2) Date: Jun. 19, 2019

(87) PCT Pub. No.: WO2018/116183
PCT Pub. Date: Jun. 28, 2018

(65) Prior Publication Data
US 2021/0130265 A1    May 6, 2021

Related U.S. Application Data

(60) Provisional application No. 62/436,586, filed on Dec. 20, 2016.

(51) Int. Cl.
*B01D 3/42* (2006.01)
*C07C 7/04* (2006.01)

(52) U.S. Cl.
CPC .............. *C07C 7/04* (2013.01); *B01D 3/4205* (2013.01); *B01D 3/4233* (2013.01)

(58) Field of Classification Search
CPC ........ B01D 3/4205; B01D 3/4233; C07C 7/04
See application file for complete search history.

(56) References Cited

U.S. PATENT DOCUMENTS 2,614,969 A * 10/1952 Morrell .................. C07C 11/20
 203/54
3,421,610 A * 1/1969 Marshall ................. C10G 7/12
 196/99

(Continued)

FOREIGN PATENT DOCUMENTS

CN    103418156 A    12/2013
CN    104661989      5/2015

(Continued)

OTHER PUBLICATIONS

Chinese Patent No. 103418156(A); Date of Publication: Dec. 4, 2013; Machine Translation; 11 Pages.

(Continued)

*Primary Examiner* — Jonathan Miller
(74) *Attorney, Agent, or Firm* — Norton Rose Fulbright US LLP

(57) ABSTRACT

A method of column control includes: passing a feed stream and a make-up stream through a column; withdrawing an overhead fraction from the column; purging at least a portion of the overhead fraction; cooling at least a portion of the overhead fraction in a heat exchanger and passing it through a reflux drum; withdrawing a purge stream and a distillate stream from the reflux drum, wherein the distillate stream has a constant flow rate; recycling at least a portion of the (Continued)

distillate stream back to the column; and passing at least a portion of the distillate stream to a downstream process.

17 Claims, 1 Drawing Sheet

(56) References Cited

U.S. PATENT DOCUMENTS

| | | | | |
|---|---|---|---|---|
| 3,428,528 A * | 2/1969 | Keeler | ............... | B01D 3/4255 203/1 |
| 3,600,282 A * | 8/1971 | Lupfer | ............... | B01D 3/4227 202/160 |
| 4,096,574 A * | 6/1978 | Christie | ............... | B01D 3/425 203/2 |
| 4,367,121 A * | 1/1983 | Furr | ................. | B01D 3/4222 203/2 |
| 6,308,532 B1 * | 10/2001 | Hopewell | ........... | C10G 70/06 62/620 |
| 2006/0135811 A1 * | 6/2006 | Seiki | ................. | B01D 3/14 562/410 |
| 2019/0345080 A1 * | 11/2019 | Rallapalli | ............. | B01D 3/00 |

FOREIGN PATENT DOCUMENTS

| | | |
|---|---|---|
| EP | 2684857 | 1/2014 |
| JP | 11137901 A | 5/1999 |
| WO | 2011126698 A2 | 10/2011 |

OTHER PUBLICATIONS

International Search Report for International Application No. PCT/IB2017/058172, International Filing Date Dec. 19, 2017, dated Mar. 26, 2018, 5 pages.
Japanese Patent No. JPH1137901(A); Date of Publication: May 25, 1999; Machine Translation; 20 Pages.
Written Opinion for international application No. PCT/IB2017/058172, international filing date Dec. 19, 2017, dated Mar. 26, 2018, 5 pages.
Sloley, A., "Effectively Control Column Pressure" The Distillation Group Inc., Chemical Engineering Progress, Jan. 2001, 11 pages.
Office Action issued in Corresponding Chinese Application No. 201780077265.3, dated May 21, 2021 (English Translation provided).

* cited by examiner

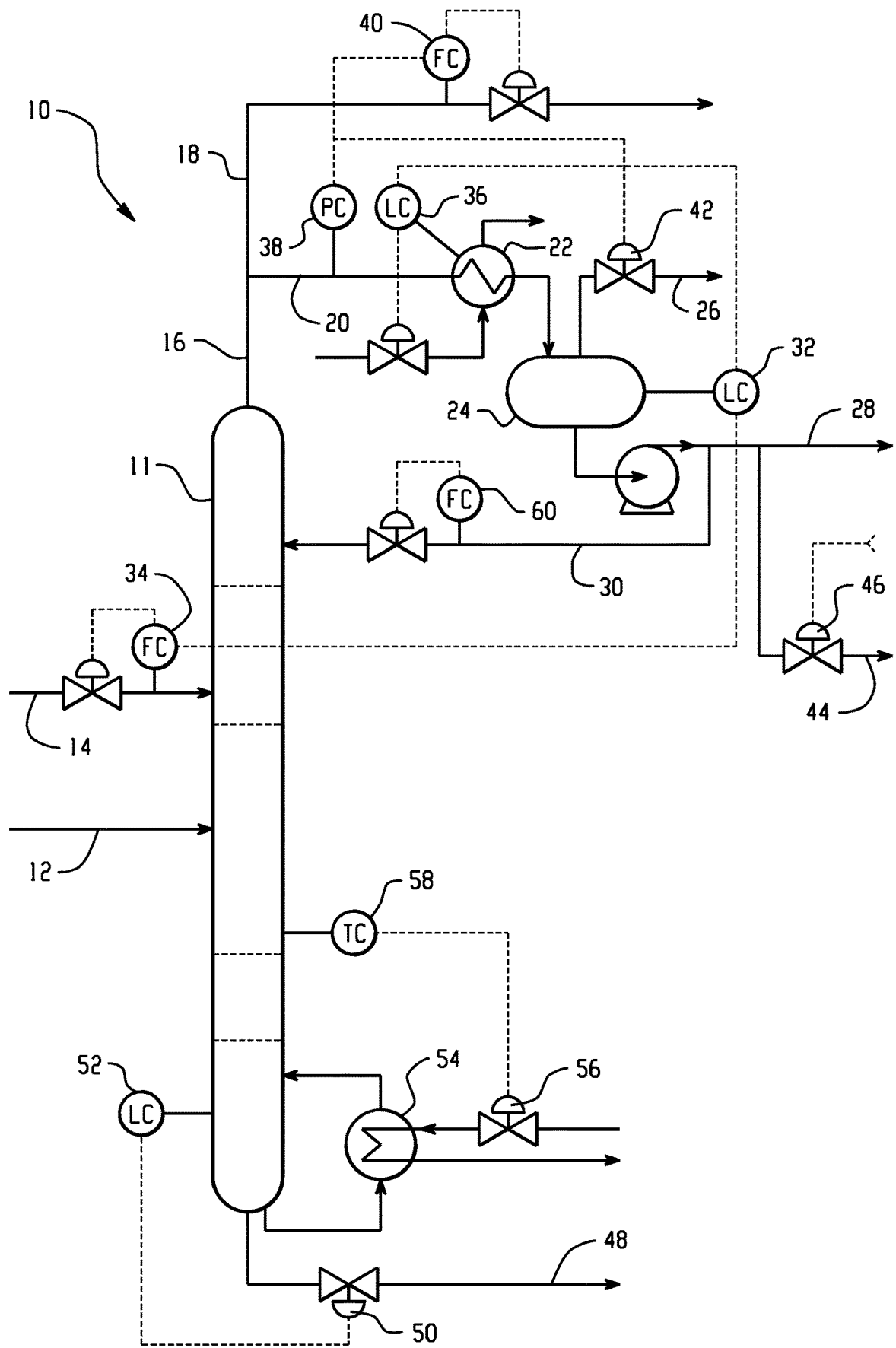

METHOD OF COLUMN CONTROL

CROSS REFERENCE TO RELATED APPLICATIONS

This application is a National Stage application of PCT/IB2017/058172, filed Dec. 19, 2017, which claims the benefit of U.S. Application No. 62/436,586, filed Dec. 20, 2016, 2016, both of which are incorporated by reference in their entirety herein.

BACKGROUND

In the production of linear alpha olefins, distillation columns are used to separate light hydrocarbons, for example, ethylene and butane, from heavier hydrocarbons. These separation processes present many engineering challenges. For example, the more demands that are put on a particular distillation column, the more difficult it can be to control the process parameters for that column. These process parameters can include temperature, pressure, and fluid level.

Unique process conditions place a large demand on column performance while also making column processing parameters difficult to control. For example, fixed reflux flow rates can be required to maintain efficient column operation. Constant distillate flow rates from reflux drums can also be required to service downstream processes. Furthermore, reflux drums can be used during intermittent intervals to supply on-demand liquid condensate to other process equipment. Accordingly, under these conditions, the fluid levels within the reflux drum can become difficult to control by standard means. Column pressure can also become difficult to control when demands on the column are high. For example, when condenser coolant must be re-purposed for the maintenance of other process equipment, it cannot be used to control column pressure and an alternative means of control must be used.

Thus, there is a need for an efficient method of column control that can allow for the maintenance and control of important process parameters, such as pressure and reflux drum level, despite the placement of high performance demands and restrictions on the column.

SUMMARY

Disclosed, in various embodiments, are methods of column control.

A method of column control, comprises: passing a feed stream and a make-up stream through a column; withdrawing an overhead fraction from the column; purging at least a portion of the overhead fraction; cooling at least a portion of the overhead fraction in a heat exchanger and passing it through a reflux drum; withdrawing a purge stream and a distillate stream from the reflux drum, wherein the distillate stream has a constant flow rate; recycling at least a portion of the distillate stream back to the column; and passing at least a portion of the distillate stream to a downstream process.

A method of column control, comprises: passing a feed stream comprising C2-C20 linear alpha olefins, solvent, spent catalyst, and catalyst deactivation agent, and a make-up stream comprising C4 linear alpha olefins through a C4/C6 distillation column; withdrawing an overhead fraction comprising C4− linear alpha olefins from the column, wherein the overhead fraction is in communication with a split-range controller; purging at least a portion of the overhead fraction, wherein the purged portion of the overhead fraction comprises C4− linear alpha olefins; cooling at least a portion of the overhead fraction in a heat exchanger and then passing it through a reflux drum, wherein the heat exchanger comprises a coolant fluid; withdrawing a purge stream comprising C4− linear alpha olefins and a distillate stream from the reflux drum, wherein the distillate stream has a constant flow rate; recycling at least a portion of the distillate stream back to the column; intermittently using at least a portion of the distillate stream as a liquid condensate supply for downstream equipment; and withdrawing a bottoms fraction comprising C6+ linear alpha olefins, solvent, spent catalyst and catalyst deactivation agent from the column.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

FIG. 1 is a schematic diagram representing a method of column control.

DETAILED DESCRIPTION

The method disclosed herein can provide an efficient method of column control that can allow for the maintenance and control of important process parameters, such as column pressure and reflux drum level, despite the placement of high performance demands and restrictions on the column. For example, the method disclosed herein can allow for fixed reflux flow rates, constant distillate flow rates from reflux drums, and the use of reflux drums during intermittent intervals to supply on-demand liquid condensate. The method can also allow condenser coolant to be re-purposed for the maintenance of other process equipment. Despite these restrictions and high demands on column performance, the present method can allow for efficient control over column pressure and reflux drum fluid level. For example, with the use of an external stream (e.g., make-up stream), the column can be controlled efficiently.

A method of column control can include passing a feed stream and a make-up stream through a column, withdrawing an overhead fraction from the column, and purging at least a portion of the overhead fraction. At least a portion of the overhead fraction can then be cooled in a heat exchanger and passed through a reflux drum. A purge stream and a distillate stream can be withdrawn from the reflux drum, where the distillate stream has a constant flow rate. At least a portion of the distillate stream can be recycled back to the column; and at least a portion of the distillate stream passed to a downstream process.

The feed stream can includes linear alpha olefins, solvent, spent catalyst, catalyst deactivation agent, or a combination comprising at least one of the foregoing.

The feed stream can include C2-C20 linear alpha olefins.

The make-up stream can include linear alpha olefins, for example C4 linear alpha olefins.

The column can include a distillation column, for example, a C4/C6 separation column.

The overhead fraction can include C4− linear alpha olefins.

The overhead fraction can include ethylene and/or butene.

The reflux drum can be in communication with a split-range controller, for example, wherein the split-range controller can include a reflux drum level controller in communication with a make-up stream flow valve and a coolant stream flow valve.

The overhead fraction can be in communication with a split-range controller. For example, the split-range controller can include a pressure controller in communication with an overhead fraction flow valve and a purge stream flow valve.

The purged portion of the overhead fraction can include C4− linear alpha olefins.

The heat exchanger can include a coolant fluid.

The purged stream from the reflux drum can include C4− linear alpha olefins.

At least a portion of the distillate stream can be intermittently passed to a downstream process.

At least a portion of the distillate stream can be intermittently used as a liquid condensate supply for downstream equipment.

A bottom fraction can be withdrawn from the column.

The bottom fraction can include C6+ linear alpha olefins, solvent, spent catalyst, catalyst deactivation agent, or a combination comprising at least one of the foregoing.

A pressure within the column can be 0 kiloPascals to 3000 kiloPascals, for example, 1000 kiloPascals to 2000 kiloPascals.

A temperature within the column is −100° C. to 300° C., for example, −40° C. to 240° C.

The method disclosed herein for column control can include a reflux drum in communication with a split-range controller, wherein the split-range controller can comprise a reflux drum level controller in communication with a make-up stream flow valve and a coolant stream flow valve. This can allow for efficient control of reflux drum fluid levels. The method can also include an overhead fraction in communication with a split-range controller, wherein the split-range controller can comprise a pressure controller in communication with an overhead fraction flow valve and a purge stream flow valve. This can allow for the efficient control of column pressure.

The method can include passing a feed stream through a column, for example, a distillation column. The feed stream can comprise hydrocarbons, for example, C2-C20 linear alpha olefins. For example, the source of the feed stream can be the product of a linear alpha olefin production process, for example, ethylene oligomerization. The feed stream can also comprise a solvent, for example, toluene, as well as spent catalyst particles and catalyst deactivating agents. A make-up stream can also be passed through the distillation column. For example, the make-up stream can comprise C4 linear alpha olefins. The make-up stream can be fed to the distillation column in a manner similar to the feed stream.

The distillation column can be, for example, a C4/C6 separation column. A pressure within the column can be 0 kiloPascals to 3000 kiloPascals, for example, 100 kiloPascals to 2500 kiloPascals, for example, 250 kiloPascals to 1000 kiloPascals, for example, 1200 kiloPascals to 2000 kiloPascals. A temperature within the column can be −100° C. to 300° C., for example, −40° C. to 240° C., for example, −25° C. to 200° C., for example, −10° C. to 150° C., for example, −5° C. to 100° C.

An overhead fraction can be withdrawn from a top portion of the distillation column. For example, the overhead fraction can comprise C4− hydrocarbons, for example, ethylene and butene. The overhead fraction can be diverted into multiple streams. For example, a portion of the overhead fraction can be purged while another portion of the overhead fraction can be passed through a heat exchanger. The heat exchanger can be a condenser that cools a portion of the overhead fraction. For example, the heat exchanger can partially condense at least a portion of the overhead fraction. The heat exchanger can be any heat exchanger that can provide the desired cooling. For example, the heat exchanger can include a spiral heat exchanger and/or a plate heat exchanger. For example, the heat exchanger can utilize a stream of coolant fluid as a cooling means.

After passing through the heat exchanger, a portion of the overhead fraction can then be passed through a reflux drum. Multiple streams can be withdrawn from the reflux drum. For example, a purge stream can be withdrawn from the reflux drum. For example, the purge stream can comprise C4− hydrocarbons that did not condense in the heat exchanger.

A distillate stream can also be withdrawn from the reflux drum. For example, the distillate stream can comprise condensed C4− hydrocarbons. The distillate stream can have a constant flow rate. A portion of the distillate stream can be recycled to the distillation column as reflux. For example, the distillate stream can be controlled by a flow controller and/or flow valve. A portion of the distillate stream can be passed to downstream processes during intermittent intervals of time. The portion of the distillate stream can, for example, be controlled by a flow valve and/or controller in communication with downstream equipment.

The distillation column can comprise multiple electrical controllers in various locations. The distillation column can also comprise multiple control valves. For example, the distillation column can comprise temperature controllers, pressure controllers, level controllers, flow valves, pressure valves, or a combination comprising at least one of the forgoing. The distillation column can also comprise various combinations of controllers and valves in communication with each other. For example, the distillation column can comprise split-range controllers.

The reflux drum can be in communication with a split-range controller. For example, the split-range controller can comprise a reflux drum level controller in communication with a make-up stream flow valve and a coolant stream flow valve. This arrangement can allow for precise control of fluid levels within the reflux drum. For example, when the reflux drum level controller detects a fluid level that is outside a desired or preferred range, the flow valves can be opened and/or closed automatically in order to compensate and correct the reflux drum fluid levels.

The overhead fraction can also be in communication with a split-range controller. For example, the split-range controller can comprise a pressure controller in communication with an overhead fraction flow valve and a purge stream flow valve. This arrangement can allow for the precise control of pressure for the distillation system. For example, when the pressure controller detects a pressure that is outside a preferred range, the corresponding flow valves can be opened and/or closed automatically to compensate and correct the pressure within the system.

A bottom fraction product stream can be withdrawn from a bottom portion of the distillation column. For example, the bottom fraction can comprise C6+ hydrocarbons. The bottom fraction product stream can also comprise a solvent, for example, toluene, as well as spent catalyst particles and catalyst deactivating agents. The flow of the bottom fraction can be controlled by a level controller located in a bottom portion of the column that is in communication with a bottom stream flow valve.

The distillation column can also comprise a reboiler heat exchanger located in a bottom portion of the column. For example, the temperature of the column can be controlled by a heat exchanger flow valve in communication with a temperature controller located in a bottom portion of the column.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Referring now to FIG. 1, this simplified schematic diagram represents a method 10 for column control. The method 10 can include passing a feed stream 12 through a distillation column 11. For example, the feed stream 12 can comprise hydrocarbons, for example, C2-C20 linear alpha olefins. The source of the feed stream 12 can be the product of a linear alpha olefin production process, for example, ethylene oligomerization. A make-up stream 14 can also be passed through the distillation column 11. For example, the make-up stream 14 can comprise C4 linear alpha olefins. The distillation column 11 can be, for example, a C4/C6 separation column.

An overhead fraction 16 can be withdrawn from a top portion of the distillation column 11. For example, the overhead fraction can comprise C4− hydrocarbons. A portion 18 of the overhead fraction can be purged. A portion 20 of the overhead fraction can be passed through a heat exchanger 22. For example, the heat exchanger 22 can be a condenser that cools the portion 20 of the overhead fraction. For example, portion 20 of the overhead fraction will be at least partially condensed after passing through exchanger 22.

The portion 20 of the overhead fraction can then be passed through a reflux drum 24. A purge stream 26 can be withdrawn from the reflux drum 24. For example, the purge stream 26 can comprise C4− hydrocarbons that did not condense in the heat exchanger 22. A distillate stream 28 can also be withdrawn from the reflux drum. For example, the distillate stream can comprise condensed C4− hydrocarbons. The distillate stream can have a constant flow rate. A portion 30 of the distillate stream 28 can be recycled back to the column 11 as reflux. For example, the portion 30 of the distillate stream 28 can be controlled by flow controller/valve 60. A portion 44 of the distillate stream 28 can be intermittently passed to downstream processes. The portion 44 of the distillate stream 28 can, for example, be controlled by flow valve/controller 46 in communication with downstream equipment.

The reflux drum 24 can be in communication with a split-range controller. For example, the split-range controller can comprise a reflux drum level controller 32 in communication with a make-up stream flow valve 34 and a coolant stream flow valve 36. The overhead fraction 16 can be in communication with a split-range controller. For example, the split-range controller can comprise a pressure controller 38 in communication with an overhead fraction flow valve 40 and a purge stream flow valve 42.

A bottom fraction product stream 48 can be withdrawn from the distillation column 11. For example, the bottom fraction 48 can comprise C6+ hydrocarbons. The flow of the bottom fraction 48 can be controlled by a level controller 52 in communication with a flow valve 50. The distillation column 11 can comprise a reboiler heat exchanger 54. For example, the temperature of the column 11 can be controlled by flow valve 56 in communication with temperature controller 58.

The processes disclosed herein include(s) at least the following aspects:

Aspect 1: A method of column control, comprising: passing a feed stream and a make-up stream through a column; withdrawing an overhead fraction from the column; purging at least a portion of the overhead fraction; cooling at least a portion of the overhead fraction in a heat exchanger and passing it through a reflux drum; withdrawing a purge stream and a distillate stream from the reflux drum, wherein the distillate stream has a constant flow rate; recycling at least a portion of the distillate stream back to the column; and passing at least a portion of the distillate stream to a downstream process.

Aspect 2: The method of Aspect 1, wherein the feed stream comprises linear alpha olefins, solvent, spent catalyst, catalyst deactivation agent, or a combination comprising at least one of the foregoing.

Aspect 3: The method of Aspect 2, wherein the feed stream comprises C2-C20 linear alpha olefins.

Aspect 4: The method of any of the preceding aspects, wherein the make-up stream comprises linear alpha olefins.

Aspect 5: The method of Aspect 4, wherein the make-up stream comprises C4 linear alpha olefins.

Aspect 6: The method of any of the preceding aspects, wherein the column is a distillation column, preferably, wherein the column is a C4/C6 separation column.

Aspect 7: The method of any of the preceding aspects, wherein the overhead fraction comprises C4− linear alpha olefins.

Aspect 8: The method of Aspect 7, wherein the overhead fraction comprises ethylene and/or butene.

Aspect 9: The method of any of the preceding aspects, wherein the reflux drum is in communication with a split-range controller, preferably, wherein the split-range controller comprises a reflux drum level controller in communication with a make-up stream flow valve and a coolant stream flow valve.

Aspect 10: The method of any of the preceding aspects, wherein the overhead fraction is in communication with a split-range controller, preferably, wherein the split-range controller comprises a pressure controller in communication with an overhead fraction flow valve and a purge stream flow valve.

Aspect 11: The method of any of the preceding aspects, wherein the purged portion of the overhead fraction comprises C4− linear alpha olefins.

Aspect 12: The method of any of the preceding aspects, wherein the heat exchanger comprises a coolant fluid.

Aspect 13: The method of any of the preceding aspects, wherein the purged stream from the reflux drum comprises C4− linear alpha olefins.

Aspect 14: The method of any of the preceding aspects, wherein at least a portion of the distillate stream is intermittently passed to a downstream process.

Aspect 15: The method of Aspect 14, wherein at least a portion of the distillate stream is intermittently used as a liquid condensate supply for downstream equipment.

Aspect 16: The method of any of the preceding aspects, further comprising withdrawing a bottoms fraction from the column.

Aspect 17: The method of Aspect 16, wherein the bottoms fraction comprises C6+ linear alpha olefins, solvent, spent catalyst, catalyst deactivation agent, or a combination comprising at least one of the foregoing.

Aspect 18: The method of any of the preceding aspects, wherein a pressure within the column is 0 kiloPascals to 3000 kiloPascals, preferably 1000 kiloPascals to 2000 kiloPascals.

Aspect 19: The method of any of the preceding aspects, wherein a temperature within the column is −100° C. to 300° C., preferably, −40° C. to 240° C.

Aspect 20: A method of column control, comprising: passing a feed stream comprising C2-C20 linear alpha olefins, solvent, spent catalyst, and catalyst deactivation agent, and a make-up stream comprising C4 linear alpha olefins through a C4/C6 distillation column; withdrawing an overhead fraction comprising C4− linear alpha olefins from the column, wherein the overhead fraction is in communication with a split-range controller; purging at least a portion of the overhead fraction, wherein the purged portion of the overhead fraction comprises C4− linear alpha olefins; cooling at least a portion of the overhead fraction in a heat exchanger and then passing it through a reflux drum, wherein the heat exchanger comprises a coolant fluid; withdrawing a purge stream comprising C4− linear alpha olefins and a distillate stream from the reflux drum, wherein the distillate stream has a constant flow rate; recycling at least a portion of the distillate stream back to the column; intermittently using at least a portion of the distillate stream as a liquid condensate supply for downstream equipment; and withdrawing a bottoms fraction comprising C6+ linear alpha olefins, solvent, spent catalyst and catalyst deactivation agent from the column.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of column control, comprising:
   passing a feed stream and a make-up stream through a column;
   withdrawing an overhead fraction from the column;
   purging at least a portion of the overhead fraction to control the pressure of the column;
   cooling at least a portion of the overhead fraction in a heat exchanger and passing it through a reflux drum to control reflux drum fluid levels;
   withdrawing a purge stream and a distillate stream from the reflux drum, wherein the distillate stream has a constant flow rate;
   recycling at least a portion of the distillate stream back to the column; and
   passing at least a portion of the distillate stream to processing equipment;
   wherein the make-up stream comprises linear alpha olefins.

2. A method of column control, comprising:
   passing a feed stream and a make-up stream through a column;
   withdrawing an overhead fraction from the column;
   purging at least a portion of the overhead fraction;
   cooling at least a portion of the overhead fraction in a heat exchanger and passing it through a reflux drum;

withdrawing a purge stream and a distillate stream from the reflux drum, wherein the distillate stream has a constant flow rate;

recycling at least a portion of the distillate stream back to the column; and passing at least a portion of the distillate stream to processing equipment, wherein the feed stream comprises linear alpha olefins, solvent, spent catalyst, catalyst deactivation agent, or a combination comprising at least one of the foregoing.

3. The method of claim 2, wherein the feed stream comprises C2-C20 linear alpha olefins.

4. The method of claim 1, wherein the make-up stream comprises C4 linear alpha olefins.

5. The method of claim 1, wherein the column is a distillation column.

6. The method of claim 1, wherein the overhead fraction comprises C4− linear alpha olefins.

7. The method of claim 6, wherein the overhead fraction comprises ethylene and/or butene.

8. The method of claim 1, wherein the reflux drum is in communication with a split-range controller.

9. The method of claim 1, wherein the overhead fraction is in communication with a split-range controller.

10. The method of claim 1, wherein the purged portion of the overhead fraction comprises C4− linear alpha olefins.

11. The method of claim 1, wherein the heat exchanger comprises a coolant fluid.

12. The method of claim 1, wherein the purged stream from the reflux drum comprises C4− linear alpha olefins.

13. The method of claim 1, further comprising withdrawing a bottoms fraction from the column.

14. The method of claim 13, wherein the bottoms fraction comprises C6+ linear alpha olefins, solvent, spent catalyst, catalyst deactivation agent, or a combination comprising at least one of the foregoing.

15. The method of claim 1, wherein a pressure within the column is 0 kiloPascals to 3000 kiloPascals.

16. The method of claim 1, wherein a temperature within the column is −100° C. to 300° C.

17. A method of column control, comprising:

passing a feed stream comprising C2-C20 linear alpha olefins, solvent, spent catalyst, and catalyst deactivation agent, and a make-up stream comprising C4 linear alpha olefins through a C4/C6 distillation column;

withdrawing an overhead fraction comprising C4− linear alpha olefins from the column, wherein the overhead fraction is in communication with a split-range controller;

purging at least a portion of the overhead fraction, wherein the purged portion of the overhead fraction comprises C4− linear alpha olefins;

cooling at least a portion of the overhead fraction in a heat exchanger and then passing it through a reflux drum, wherein the heat exchanger comprises a coolant fluid;

withdrawing a purge stream comprising C4− linear alpha olefins and a distillate stream from the reflux drum, wherein the distillate stream has a constant flow rate;

recycling at least a portion of the distillate stream back to the column;

intermittently using at least a portion of the distillate stream as a liquid condensate supply for processing equipment; and withdrawing a bottoms fraction comprising C6+ linear alpha olefins, solvent, spent catalyst and catalyst deactivation agent from the column.

* * * * *